United States Patent [19]

Nishimura et al.

[11] 4,162,316
[45] Jul. 24, 1979

[54] 1-SUBSTITUTED-4-(1,2-DIPHENYLETHYL)-PIPERAZINE DERIVATIVES AND COMPOSITIONS CONTAINING THE SAME

[75] Inventors: Haruki Nishimura, Ikeda; Hitoshi Uno, Takatsuki; Kagayaki Natsuka, Ibaraki; Noriaki Shimokawa, Nagaokakyo; Masanao Shimizu, Kobe; Hideo Nakamura, Tenri, all of Japan

[73] Assignee: Dainippon Pharmaceutical Co., Ltd., Osaka, Japan

[21] Appl. No.: 821,918

[22] Filed: Aug. 4, 1977

Related U.S. Application Data

[62] Division of Ser. No. 663,158, Mar. 2, 1976, Pat. No. 4,080,453.

[30] Foreign Application Priority Data

Mar. 12, 1975 [JP] Japan ................... 50-30559
Jul. 22, 1975 [JP] Japan ................... 50-89849
Jul. 22, 1975 [JP] Japan ................... 50-89851
Jul. 22, 1975 [JP] Japan ................... 50-89852
Jul. 22, 1975 [JP] Japan ................... 50-89853
Nov. 27, 1975 [JP] Japan ................... 50-142496

[51] Int. Cl.² ................... C07D 241/04; A61K 31/495
[52] U.S. Cl. ................... 424/250; 544/392
[58] Field of Search ................... 260/268 R; 544/392; 424/250

[56] References Cited

U.S. PATENT DOCUMENTS 2,858,312  10/1958  Olin ................... 260/268 R

FOREIGN PATENT DOCUMENTS 242151  9/1965  Austria ................... 260/268 R

OTHER PUBLICATIONS

Nishimura et al., C.A. 84, 180286p (1976) Abstr. of Jap. Pat. No. 75,123,685, 9/29/75.
Nishimura et al., C.A. 83, 193387b (1975) Abstr. of Ger. Offen. No. 2,502,729, 7/24/75.

Primary Examiner—Donald G. Daus
Assistant Examiner—D. B. Springer
Attorney, Agent, or Firm—Stevens, Davis, Miller & Mosher

[57] ABSTRACT

1-Substituted-4-(1,2-diphenylethyl)piperazine derivatives of the formula:

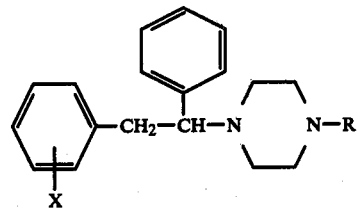

wherein X is 2- or 3-hydroxy, 2-methoxy, 3-methyl, 3-alkoxy having 1 to 4 carbon atoms, or 2- or 3-alkanoyloxy having 2 to 5 carbon atoms; R is allyl, 3-hydroxyisoamyl, 3-methyl-2-butenyl, 3-methyl-3-butenyl, propyl, an unsubstituted monocycloalkyl having 5 to 8 carbon atoms, 2-chlorophenyl, or a phenyl substituted by hydroxy or methoxy; with proviso that when X is a substituent at position 2, R is cyclohexyl and when X is 3-methyl, R is 2-methoxyphenyl or an unsubstituted monocycloalkyl having 6 to 8 carbon atoms, and their pharmaceutically acceptable salts, and the preparation thereof, and analgesic or antitussive compositions containing the same as the essentially active ingredient.

15 Claims, No Drawings

1-SUBSTITUTED-4-(1,2-DIPHENYLETHYL)PIPERAZINE DERIVATIVES AND COMPOSITIONS CONTAINING THE SAME

This is a Division of application Ser. No. 663,158 filed Mar. 2, 1976, now U.S. Pat. No. 4,080,453.

The present invention relates to novel, pharmaceutically active 1-substituted-4-(1,2-diphenylethyl)piperazine derivatives and their pharmaceutically acceptable salts and the preparation thereof and pharmaceutical compositions containing the same as the essentially active ingredient. More particularly, it relates to 1-substituted-4-(1,2-diphenylethyl)piperazine derivatives of the following formula:

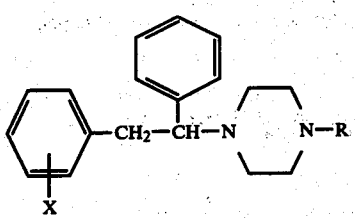

wherein X is 2- or 3-hydroxy, 2-methoxy, 3-methyl, 3-alkoxy having 1 to 4 carbon atoms, or 2- or 3-alkanoyloxy having 2 to 5 carbon atoms; and R is allyl, 3-hydroxyisoamyl, 3-methyl-2-butenyl, 3-methyl-3-butenyl, propyl, an unsubstituted monocycloalkyl having 5 to 8 carbon atoms, 2-chlorophenyl, or a phenyl substituted by hydroxy or methoxy; with proviso that when X is a substituent at position 2, R is cyclohexyl, and when X is 3-methyl, R is 2-methoxyphenyl or an unsubstituted monocycloalkyl having 6 to 8 carbon atoms, and their pharmaceutically acceptable salts, and the preparation thereof, and pharmaceutical compositions containing one or more compounds as set forth above as the essentially active ingredient.

The present compounds have an asymmetric carbon in the molecule, and therefore, optical isomers exist. The present invention includes all these optically active isomers and the racemic compounds thereof.

Some compounds having an analogous structure to that of the present compounds have been already described in Japanese Patent Publication Nos. 6304/1972 and 188/1974 and The Japanese Journal of Pharmacology, Vol. 22, page 88 Apr. 27, 1972), etc. These known compounds have been prepared by some of the present inventors, and some compounds among them have a comparatively potent analgesic activity. However, such compounds have a morphine-like physical dependence liability or too strong toxicity.

It has, hitherto, never been known that these piperazine derivatives have an antitussive activity. As the results of the intensive studies of the present inventors, it has been found that the novel piperazine derivatives of the formula [I] and their pharmaceutically acceptable salts show potent analgesic or valuable antitussive activities. Particularly, it has been found that the compounds of the formula [I] wherein X is 3-hydroxy or 3-alkanoyloxy having 2 to 5 carbon atoms, or X is 3-alkoxy having 1 to 4 carbon atoms and R is 3-methyl-2(or 3)-butenyl or 2-methoxyphenyl show potent analgesic activity, and further that the compounds of the formula [I] wherein X is a substituent at position 2 or 3-methyl show an valuable antitussive activity. The l-isomers of these compounds are particularly preferable because of the lack of morphine-like physical dependence liability. Thus, the compounds of the present invention are useful as an analgesic or antitussive.

The compounds where R group in the formula [I] is hydrogen are also novel and are useful as an intermediate for the preparation of the compounds of the formula [I].

An object of the present invention is to provide novel piperazine derivatives and their pharmaceutically acceptable salts having useful pharmacological activities.

Another object of the invention is to provide a process for the preparation of the piperazine derivatives and their pharmaceutically acceptable salts.

A further object of the invention is to provide a pharmaceutical composition containing the compound as set forth above as the active ingredient.

Still further object of the invention is to provide the use of the compound as set forth above as an analgesic or antitussive.

These and other objects of the invention will be apparent from the description hereinafter.

The compounds of the present invention include those represented by the formula [I] as shown hereinbefore and their pharmaceutically acceptable salts. Especially suitable compounds as an analgesic of the present invention are as follows:

1-1-(3-methyl-2-butenyl)-4-[2-(3-hydroxyphenyl)-1-phenylethyl]piperazine, 1-1-(3-methyl-2-butenyl)-4-[2-(3-methoxyphenyl)-1-phenylethyl]piperazine, 1-1-cyclohexyl-4-[2-(3-hydroxyphenyl)-1-phenylethyl]-piperazine, and 1-1-(2-methoxyphenyl)-4-[2-(3-methoxyphenyl)-1-phenylethyl]piperazine, and their pharmaceutically acceptable acid addition salts.

Especially suitable compounds as an antitussive of the present invention are as follows:

1-1-cyclohexyl-4-[1-phenyl-2-(3-tolyl)ethyl]piperazine, dl-1-cyclohexyl-4-[1-phenyl-2-(3-tolyl)ethyl]piperazine, 1-1-cyclohexyl-4-[2-(2-hydroxyphenyl)-1-phenylethyl-]-piperazine, and 1-1-(2-methoxyphenyl)-4-[1-phenyl-2-(3-tolyl)ethyl]-piperazine, and their pharmaceutically acceptable acid addition salts.

The activities of the present compounds are demonstrated by the following experimental tests.

(1) Analgesic acitivity:

(i) D'Amour-Smith method (cf. F. E. D'Amour and D. L. Smith, J. Pharmacol. Exp, Ther., Vol. 72, page 74, 1941)

Thermal pain was induced by radiating heat light on the tail blacked with a black ink of male mice of ddN strain, weighing 9 to 12 g, using the modified apparatus of D'Amour-Smith. The analgesic $Ed_{50}$-value (mg/kg) was calculated from the number of positive animals showing the response time prolonged more than 100% compared with each preceding value.

(ii) Haffner method (cf. F. Haffner, Deut. Med. Wochschr., Vol. 55, page 731, 1929)

Mechanical pain was induced by pressing the tail of male rats of Wistar strain, weighing 90 to 110 g, using the modified appratus of Haffner. The analgesic $Ed_{50}$-value (mg/kg) was calculated from the number of positive animals showing pain threshold of 40 mm or more (normal value is about 20 mm).

(iii) Phenylquinone method (cf. E. Siegmund, R. Cadmus and G. Lu, Proc. Soc. Exptl. Biol. Med., Vol. 95, page 729, 1957)

Chemical pain was induced by an intraperitoneal injection of 0.1 ml/10 g body weight of 0.03% phenylquinone in 5% aqueous ethanol in female mice, weighing 18 to 22 g of ddN strain. Drugs were given 30 minutes before challenge of phenylquinone.

The test results are shown in the following Tables 1 to 3.

Table 1

| Test compound | Analgesic activity ED$_{50}$-value (mg/kg) | |
|---|---|---|
| | D'Amour-Smith method (s.c.) | Phenylquinone method (p.o.) |
| 1 | 0.40 | 0.20 |
| 2 | 25.1 | 13.6 |
| 3 | 0.038 | 0.28 |
| 4 | 8.64 | 3.62 |
| 5 | 1.87 | — |
| 6 | ca. 0.5 | — |
| 7 | 14.0 | 0.94 |
| 8 | — | 18.8 |
| 9 | 1.57 | 5.99 |
| Reference compound | | |
| A | > 160 (inactive) | — |
| B | ≧ 70 (toxic dose) | ≧ 100 |
| C | > 160 | — |
| D | 2.39 | 4.20 |

[Note]: *The test compounds are as follows:
1: dl-1-(3-Methyl-2-butenyl)-4-[2-(3-hydroxyphenyl)-1-phenylethyl]piperazine . 2HCl
2: l-1-(3-Methyl-2-butenyl)-4-[2-(3-hydroxyphenyl)-1-phenylethyl]piperazine . 2HCl
3: dl-1-(3-Methyl-3-butenyl)-4-[2-(3-hydroxyphenyl)-1-phenylethyl]piperazine . 2HCl . 1/2H$_2$O
4: dl-1-Allyl-4-[2-(3-hydroxyphenyl)-1-phenylethyl]piperazine . 2HCl . C$_2$H$_5$OH
5: dl-1-Propyl-4-[2-(3-hydroxyphenyl)-1-phenylethyl]piperazine . 2HCl . 1/2H$_2$O
6: dl-1-(3-Hydroxyisoamyl)-4-[2-(3-hydroxyphenyl)-1-phenylethyl]piperazine . 2HCl . 11/2H$_2$O
7: dl-1-(3-Methyl-2-butenyl)-4-[2-(3-methoxyphenyl)-1-phenylethyl]piperazine . 2HCl
8: l-1-(3-Methyl-2-butenyl)-4-[2-(3-methoxyphenyl)-1-phenylethyl]piperazine . 2HCl
9: dl-1-(3-Methyl-3-butenyl)-4-[2-(3-methoxyphenyl)-1-phenylethyl]piperazine . 2HCl . 1/2H$_2$O
A: dl-1-Allyl-4-(1,2-diphenylethyl)piperazine . 2HCl (disclosed in Japanese Patent Publication No. 6304/1972)
B: dl-1-Isobutyl-4-(1,2-diphenylethyl)piperazine . 2HCl (disclosed in Japanese Patent Publication No. 6304/1972)
C: dl-1-Allyl-4-[2-(3-chlorophenyl)-1-phenylethyl]piperazine . 2HCl
D: Morphine hydrochloride Table 2

| Test compound* | Analgesic activity ED$_{50}$-value (mg/kg) D'Amour-Smith method (s.c.) |
|---|---|
| 10 | 0.065 |
| 11 | 0.028 |
| 12 | ca. 0.07 |
| 13 | 0.47 |
| 14 | Insoluble [ca. 2.1 (i.p.)] |
| 15 | ca. 0.8 |
| 16 | ca. 16.0 |
| 17 | 1.41 |
| 18 | 1.40 |
| 19 | 4.45 |
| Reference compound | |
| E | >160 |
| F | 15.4 |
| G | Insoluble [>80(i.p.)] |
| D | 2.39 |

[Note]: *The Reference compound D is as defined in Table 1, and other Reference compounds and the test compounds are as follows:
10: dl-1-(2-Methoxyphenyl)-4-[2-(3-hydroxyphenyl)-1-phenylethyl]piperazine . 2HCl . 1/2H$_2$O
11: d-1-(2-Methoxyphenyl)-4-[2-(3-hydroxyphenyl)-1-phenylethyl]piperazine . 2HCl . 1/2H$_2$O
12: dl-1-(2-Hydroxyphenyl)-4-[2-(3-hydroxyphenyl)-1-phenylethyl]piperazine . 2HBr
13: dl-1-(3-Methoxyphenyl)-4-[2-(3-hydroxyphenyl)-1-phenylethyl]piperazine . 2HCl
14: dl-1-(3-Hydroxyphenyl)-4-[2-(3-hydroxyphenyl)-1-phenylethyl]piperazine . 2HCl
15: dl-1-(4-Methoxyphenyl)-4-[2-(3-hydroxyphenyl)-1-phenylethyl]piperazine . 2HCl
16: l-1-(2-Methoxyphenyl)-4-[2-(3-methoxyphenyl)-1-phenylethyl]piperazine . 2HCl . 1/2H$_2$O
17: dl-1-(2-Chlorophenyl)-4-[2-(3-hydroxyphenyl)-1-phenylethyl]piperazine . HCl . 1/2H$_2$O
18: dl-1-(2-Methoxyphenyl)-4-[2-(3-methoxyphenyl)-1-phenylethyl]piperazine . 2HCl . 1/2H$_2$O
19: dl-1-(2-Methoxyphenyl)-4-[2-(3-ethoxyphenyl)-1-phenylethyl]piperazine . 2HCl . 1/2H$_2$O
E: dl-1-Phenyl-4-(1,2-diphenylethyl)piperazine . 2HCl (disclosed in Japanese Patent Publication No. 6304/1972)
F: dl-1-(2-Methoxyphenyl)-4-(1,2-diphenylethyl)piperazine . 2HCl . 1/2H$_2$O (disclosed in Japanese Patent Publication No. 6304/1972)
G: dl-1-(2-Methoxyphenyl)-4-[2-(3-chlorophenyl)-1-phenylethyl]piperazine . 2HCl Table 3

| Test compound | Analgesic activity ED$_{50}$-value (mg/kg) (s.c.) | |
|---|---|---|
| | D'Amour-Smith method | Haffner method |
| 20 | 0.14 | 0.06 |
| 21 | 0.056 | — |
| 22 | 3.12 | 0.26 |
| 23 | 0.11 | <0.04 |
| 24 | 0.18 | — |
| 25 | 0.95 | — |
| 26 | 0.21 | — |
| Reference compound | | |
| H | 3.09 | 0.73 |
| I | 1.92 | 0.73 |
| J | 50.7 | — |
| K | ≧160 | — |
| D | 2.39 | 1.17 |

[Note]: * The compound D is as defined in Table 1, and other Reference compounds and the Test compounds are as follows:
20: dl-1-Cyclohexyl-4-[2-(3-hydroxyphenyl)-1-phenylethyl]-piperazine . 2HBr
21: d-1-Cyclohexyl-4-[2-(3-hydroxyphenyl)-1-phenylethyl]-piperazine . 2HCl
22: l-1-Cyclohexyl-4-[2-(3-hydroxyphenyl)-1-phenylethyl]-piperazine . 2HCl
23: dl-1-Cycloheptyl-4-[2-(3-hydroxyphenyl)-1-phenylethyl]-piperazine . 2HBr
24: dl-1-Cyclooctyl-4-[2-(3-hydroxyphenyl)-1-phenylethyl]-piperazine . 2HBr
25: dl-1-Cyclopentyl-4-[2-(3-hydroxyphenyl)-1-phenylethyl]-piperazine . 2HCl
26: dl-1-Cyclohexyl-4-[1-phenyl-2-(3-propionyloxyphenyl)ethyl]-piperazine . 2HCl
H: dl-1-Cyclohexyl-4-(1,2-diphenylethyl)piperazine . 2HCl (disclosed in Japanese Patent Publication No. 6304/1972)
I: d-1-Cyclohexyl-4-(1,2-diphenylethyl)piperazine . 2HCl (disclosed in Japanese Patent Publication No. 188/1974)
J: l-1-Cyclohexyl-4-(1,2-diphenylethyl)piperazine . 2HCl (disclosed in Japanese Patent Publication No. 138/1974)
K: dl-1-Cyclohexyl-4-[2-(3-chlorophenyl)-1-phenylethyl]-piperazine . 2HCl (2)Antitussive activity (cf. K. Takagi, H. Fukuda and K. Yano, Yakugakuzasshi, Vol. 80, page 1497, 1960):

Male guinea-pigs, weighing 400 to 600 g, were lightly anaesthetized by intraperitoneal injection of pentobarbital sodium (20 mg/kg). Coughs were caused by successive mechanical stimulations of 5 times with a rabbit whisker on the mucosa of the exposed trachea of the animals 5, 10, 15, 30, 45, 60, 75, 90 and 120 minutes after the intraperitoneal injection of each test compound. Antitussive effect was evaluated by all or none of the cough. When no cough per 5 successive stimulations was observed at any time during 120 minutes, the effect was considered to be significant.

The 50% antitussive dose (Ed$_{50}$) was calculated from the effective rates by the Lithchfield-Wilcoxon method. The test results are shown in the following Table 4.

Table 4

| Test compound* | Antitussive activity ED$_{50}$-value (mg/kg) i.p. |
|---|---|
| 27 | 4.55 |
| 28 | 6.70 |
| 29 | ca. 6.0 |
| 30 | ca. 8.0 |
| 31 | ca. 6.0 |
| 32 | ca. 6.0 |
| Reference compound L | 12.17 |

[Note]: * The test compounds are as follows:
27: dl-1-Cyclohexyl-4-[1-phenyl-2-(3-tolyl)ethyl]piperazine . 2HCl
28: l-1-Cyclohexyl-4-[1-phenyl-2-(3-tolyl)ethyl]piperazine . 2HCl
29: dl-1-Cyclooctyl-4-[1-phenyl-2-(3-tolyl)ethyl]piperazine . 2HCl
30: l-1-Cyclohexyl-4-[2-(2-hydroxyphenyl)-1-phenylethyl]-piperazine . 2HCl
31: dl-1-(2-Methoxyphenyl)-4-[1-phenyl-2-(3-tolyl)ethyl]-piperazine . 2HCl . ½H$_2$O
32: l-1-(2-Methoxyphenyl)-4-[1-phenyl-2-(3-tolyl)ethyl]piperazine . 2HCl . ½H$_2$O
L: Codeine phosphate (3) Physical dependence liability:

Substitution test in morphine-dependent rats (cf. O. J. Lorenzetti and L. F. Sancilio, Arch. int. Pharmacodyn., Vol. 183, page 391, 1970; S. Nurimoto, Japan. J. Pharmacol., Vol. 23, page 401, 1973; and H. Nakamura et al, Folia Pharmacol. Japonica, Vol. 71, page 105P, 1975).

Male rats of Wistar strain, weighing 200 to 250 g, received morphine hydrochloride subcutaneously twice daily. The initial dose of 20 mg/kg was increased weekly by 20 mg/kg until a maintenance of 100 mg/kg X 2/day was attained. The animals received two subcutaneous or oral administrations of a test compound instead of morphine hydrochloride. The withdrawal symptoms were determined and the percent reduction of each withdrawal symtom was calculated from the scores of test compound and vehicle control groups.

As the results, the compound Nos. 2, 8, 16 and 22 did not show the depression of withdrawal symptoms, i.e. the morphine-like physical dependence liability.

The compounds [I] and their pharmaceutically acceptable salts of the present invention may be used as medicines, for example, in the form of pharmaceutical preparations containing the compound in admixture with an organic or inorganic, solid or liquid pharmaceutical adjuvants suitable for oral or parenteral administration. Pharmaceutically acceptable adjuvants are substances that do not react with the compounds, for example, water, gelatin, lactose, starch, cellulose, preferably microcrystalline cellulose, sodium caboxymethyl cellulose, calcium carboxymethyl cellulose, methyl cellulose, sorbitol, magnesium stearate, talc, vegetable oils, benzyl alcohol, gums, propylene glycol, polyalkylene glycols, methyl-paraben and other known medicinal adjuvants. The pharmaceutical preparations may be, for example, powder, tablets, suppositories, or capsules, or in liquid form as solutions, suspensions, or emulsions. When administered as liquids, conventional liquid carriers such as syrup, peanut oil, olive oil, water and the like can be used. For intravenous or intramuscular injection, those in acid addition salt form are employed after dissolving in water, if necessary, followed by buffering or making isotonic with glucose, saline or the like. These preparations may further contain other therapeutically valuable substances. The preparations are prepared by conventional methods.

A clinical dosage of the compound [I] or its pharmaceutically acceptable salt depends on body weight, age and administration routes, but it is generally in the range of 0.1 to 200 mg/day, preferably of 0.5 to 100 mg/day.

The compounds of the formula [I] and their pharmaceutically acceptable salts of the present invention can be prepared by the following processes (1) to (6).

Process (1):

The compounds can be prepared by reacting a compound of the formula:

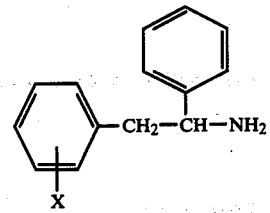

[II]

wherein X is as defined above, with a compound of the following formula:

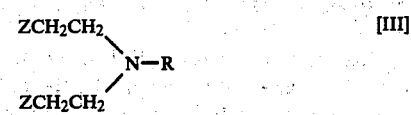

[III]

wherein Z is a residue of reactive ester of alcohol, such as halogen (e.g. chlorine or bromine), arylsulfonyloxy (e.g. p-toluenesulfonyloxy or benzenesulfonyloxy) or alkylsulfonyloxy (e.g. methanesulfonyloxy), and R is as defined above, or its salts.

The reaction of the Process (1) may be carried out by heating a mixture of the compound [III] with an equimolar or excess amount of the compound [II] in the presence or absence of a solvent, such as an aliphatic alcohol (e.g. aqueous or anhydrous ethanol or isopropanol), an aromatic hydrocarbon (e.g. toluene or xylene), an ether (e.g. dioxane), dimethylformamide, or dimethyl sulfoxide. Suitable reaction temperature may be 60 to 170° C., and the reaction may usually be carried out at a reflux temperature.

The reaction may be also carried out in the presence of a basic material, such as an alkali metal hydrogen carbonate (e.g. sodium hydrogen carbonate or potassium hydrogen carbonate), an alkali metal carbonate (e.g. sodium carbonate or potassium carbonate), or an organic base (e.g. triethylamine). The reactant of the formula [II] may also be utilized as the basic material by using in an excess amount.

The starting material [II] in the above Process (1) can be prepared in a similar manner as described in Archiv der Pharmazie, Vol. 274, page 153, 1936 and British Patent Specification No. 1,300,428 (1972).

Besides, the other starting material [III] can be prepared in a similar manner as described in Journal of American Chemical Society, Vol. 73, page 3635, 1951; Journal of Chemical Society, page 183, 1949; and Journal of Medicinal Chemistry, Vol. 6, page 882, 1963, for instance, by reacting N-cyclohexyldiethanolamine or its salt with a conventional halogenating agent, such as thionyl chloride, thionyl bromide, or with a conventional sulfonating agent, such as p-toluenesulfonyl chloride, benzenesulfonyl chloride, or methanesulfonyl chloride.

Process (2):

The compounds [I] and their pharmaceutically acceptable salts can be prepared by reacting a compound of the following formula:

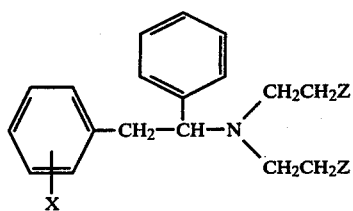

[IV]

wherein X and Z are as defined above, or its salts with a compound of the formula:

H₂N-R  [V]

wherein R is as defined above.

The reaction of the Process (2) may be carried out by heating a mixture of the compound [IV] with an equimolar or excess amount of the compound [V] in the presence or absence of a solvent in a similar manner as described in Process (1).

The starting material [IV] in the above Process (2) can be prepared, for example, by the following process.

3-(2-Hydroxyethyl)-2-phenyloxazolidine is reacted with a compound of the formula:

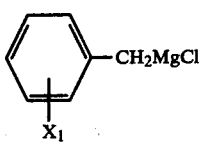

[VI]

wherein X₁ is 2-methoxy, 3-methyl, or 3-alkoxy having 1 to 4 carbon atoms, in an inert solvent to give a compound of the formula:

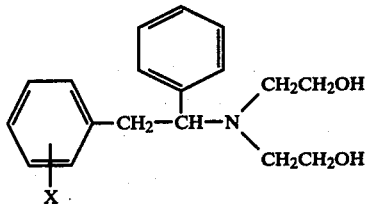

[VII]

wherein X₁ is as defined above, or its salt. Subsequently, the compound [VII] or its salt thus obtained is reacted with a coventional halogenating or sulfonating agent as described in the Process (1) to give the desired compound [IV] wherein X is X₁, i.e. 2-methoxy, 3-methyl, of 3-alkoxy having 1 to 4 carbon atoms. When the compound [IV] thus obtained (X is methoxy) is subjected to cleavage of the ether linkage by treating it with a cleavage agent for splitting ether, the desired compound [IV] wherein X is hydroxy can be obtained. Examples of the cleavage agents for splitting ethers include Lewis acids (e.g. aluminum chloride, aluminum bromide or boron tribromide) and hydrohalogenic acid (e.g. hydrobromic acid, hydroiodic or hydrochloric acid). Further, when the compound [IV] wherein X is 3-hydroxy is reacted with an alkanoylating agent in the conventional manner, the desired compound [IV] wherein X is 3-alkanoyloxy having 2 to 5 carbon atoms can be obtained. Besides, the compound [IV] may also be obtained by reacting the compound [II] with ethylene oxide, followed by reacting with a halogenating or sulfonating agent as mentioned above.

Process (3):

The compound of the following formula:

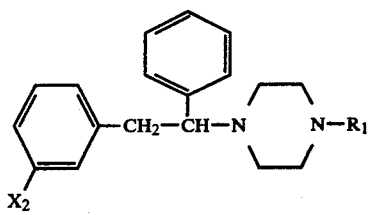

[VIII]

wherein X₂ is hydroxy or an alkoxy having 1 to 4 carbon atoms; and R₁ is allyl, 3-hydroxyisoamyl, 3-methyl-2-butenyl, 3-methyl-3-butenyl or propyl, and its pharmaceutically acceptable salt can be prepared by reacting a compound of the following formula:

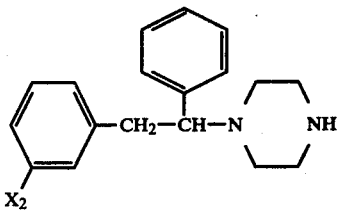

[IX]

wherein X₂ is as defined above, with a compound of the following formula:

Z—R₁  [X]

wherein R₁ and Z are as defined above.

The reaction of the Process (3) may be carried out by heating a mixture of the compound [IX] with an equimolar or slightly excess amount of the compound [X] in the presence or absence of solvent in a similar manner as described in Process (1).

The starting material [IX] in the above Process (3) can be prepared, for instance, by the following process.

A compound [II] wherein X is X₂ is reacted with N-benzyl-2,2'-dichlorodiethylamine hydrochloride [J. Amer. Chem. Soc., Vol. 73, page 3635 (1951)] at an elevated temperature in dimethylformamide in the presence of sodium hydrogen carbonate to give a compound of the formula:

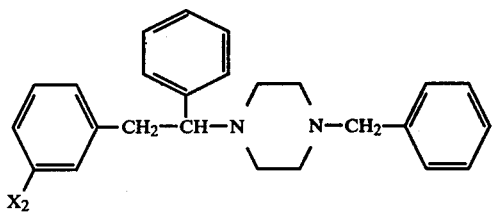

[XI]

wherein X₂ is as defined above, and subjecting the resulting compound [XI] or its salt to a catalytic reduction in acetic acid in the presence of palladiumcarbon to give the desired compound [IX].

Process (4):

The compound of the following formula:

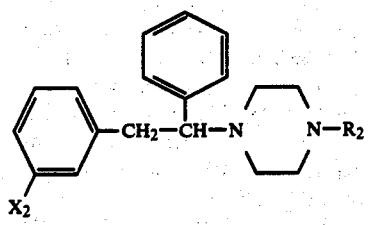

[XII]

wherein R₂ is 3-methyl-2-butenyl or 3-methyl-3-butenyl; and X₂ is as defined above, and its pharmaceutically acceptable salt can also be prepared by reducing a compound of the formula:

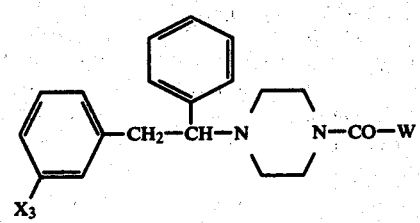

[XIII]

wherein W is 2-methyl-1-propenyl or 2-methyl-2-propenyl; and X₃ is hydroxy, an alkoxy having 1 to 4 carbon atoms or 3-methyl-2 3)-butenoyloxy.

The reaction may be carried out by a conventional reduction method, for instance, by reducing the compound [XIII] with a metal hydride complex (e.g. lithium aluminum hydride) or diborane in an appropriate solvent (e.g. ethyl ether, tetrahydrofuran, dioxane, or a mixture of one or more of these solvents with benzene). The reaction may usually be carried out at room temperature or an elevated temperature, preferably at a reflux temperature of the reaction mixture. In this reaction, the O-acyl group is reductively removed.

The starting material [XIII in the above Process (4) can be prepared by reacting the compound [IX] with a compound of the formula:

W—CO—Cl          [XIV]

wherein W is as defined above, at room temperature or an elevated temperature in an inert solvent (e.g. methanol, dimethylsulfoxide or benzene) in the present of a base (e.g. triethylamine or potassium carbonate).

Process (5):
The compound of the following formula:

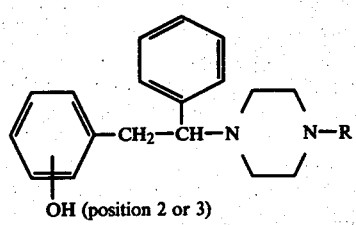

[XV]

OH (position 2 or 3)

wherein R is as defined above, and its pharmaceutically acceptable salt can also be prepared by the following processes.

(i) Process (5-1):
A compound of the following formula:

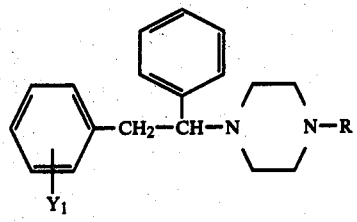

[XVI]

wherein Y₁ is 2- or 3-alkoxy having 1 to 7 carbon atoms or 2- or 3-benzyloxy; R is those as defined above other than methoxypheny, or its salt is subjected to cleavage of the ether linkage by treating it with a cleavage agent for splitting ethers at room temperature or an elevated temperature, preferably at a reflux temperature, in the presence or absence of a solvent (e.g. water, acetic acid, methylene chloride, toluene, xylene, nitrobenzene, or chlorobenzene) to give the desired compound [XV].

The cleavage agents for splitting ethers include Lewis acids (e.g. aluminum chloride, aluminum bromide or boron tribromide) and hydrohalogenic acid (e.g. hydrobromic acid, hydroiodic acid, or hydrochloric acid).

In the above reaction, when the R group in the formula [XVI] is 3-methyl-2-butenyl, the compound [XV] wherein R is 3-methyl-3-butenyl or 3-hydroxyisoamyl may occasionally be by-produced.

(ii) Process (5-2):
A compound of the following formula:

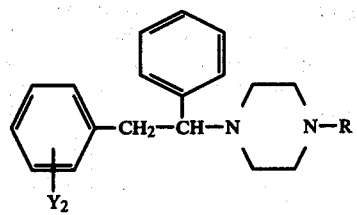

[XVII]

wherein Y₂ is 2- or 3-benzyloxy; R is those as defined above other than 3-methyl-2-butenyl,3-methyl-3-butenyl or allyl, or its salt is subjected to hydrogenolysis, for instance, by catalytically reducing it with an equimolar or slightly excess amount of hydrogen in the presence of a catalyst in a solvent at room temperature or an elevated temperature under atmospheric or elevated pressure to give the desired compund [XV]. The catalyst used therein includes palladium-carbon, Raney nickel, platinum black, or the like, and the solvent includes aqueous or anhydrous alkanol (e.g. methanol, or ethanol), water, acetic acid, dioxane, or the like.

(iii) Process (5-3):
A compound of the following formula:

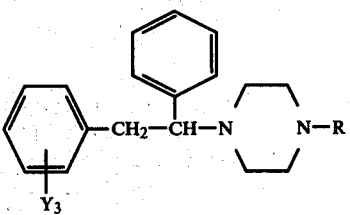

[XVIII]

wherein Y₃ is 2- or 3-acyloxy; R is as defined above, or its salt is subjected to hydrolysis to give the desired compound [XV].

The reaction may be carried out in an aqueous solvent under an acidic or alkaline condition, for instance, in a diluted aqueous solution of an alkali metal hydroxide (e.g. sodium hydroxide, or potassium hydroxide) or a mineral acid (e.g. hydrochloric acid, hydrobromic acid, or sulfuric acid), or in a mixed solvent of water with an alkanol or acetic acid at a temperature from room temperature to 120° C., preferably at a reflux temperature.

The "acyloxy" denotes a lower alkanoyloxy having 2 to 5 carbon atoms (e.g. acetoxy, propionyloxy, butyroyloxy, or isobutyroyloxy), an aroyloxy (e.g. benzoyloxy or p-toluoyloxy) or an aralkanoyloxy having 2 to 3 carbon atoms in the alkanoyl moiety (e.g. phenylacetoxy).

The starting materials [XVI - XVIII] in the above Process (5) may be prepared in a similar manner as described in the above Process (1) or Process (2).

Process (6):

The compound of the following formula:

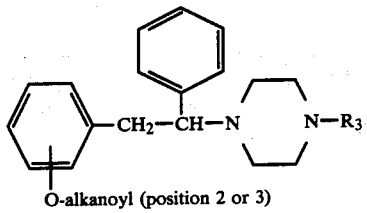

O-alkanoyl (position 2 or 3)

[XIX]

wherein the alkanoyloxy has 2 to 5 carbon atoms, and R₃ is the ame as those for R as defined above other than hydroxyphenyl and 3-hydroxyisoamyl, or its pharmaceutically acceptable salt is prepared by reacting a compound of the formula:

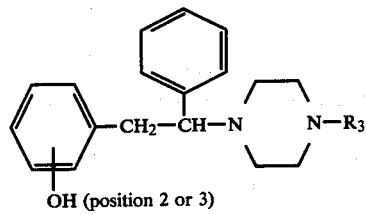

OH (position 2 or 3)

[XX]

wherein R₃ is as defined above, or its salt with an alkanoylating agent.

The alkanoylation of the compound [XX] to the compound [XIX] may be carried out by a conventional method, and preferably, by reacting the compound [XX] with a carboxylic acid or its reactive derivative, such as an acid halide or an acid anhydride in the presence or absence of a solvent. Suitable examples of the carboxylic acid are acetic acid, propionic acid, butyric acid, isobutyric acid, or the like. As the solvent, there may be used any solvent which does not give any undesirable effect on the reaction, and for instance, an inert solvent such as pyridine, benzene, toluene or dioxane may be used. Suitable reaction temperature may be 0° to 150° C., and the reaction may usually be carried out at a reflux temperature.

In the above processes of the preparation of the present invention, the starting materials and the intermediates may be either in the racemic form or in the optically active form when they have an asymmetric carbon in the molecule. When the racemic compound is used as the starting material or the intermediate, the final compound [I] is also obtained in the form of racemic compound. Besides, when the optically active compound is used as the starting material or the intermediate, the final compound [I] is also obtained in the form of the optically active compound. The optically active compound [I] can also be prepared by resolving the racemic compound [I] with an optically resolving agent, for instance, optically active tartaric acid monoanilides (e.g. 2'-nitrotartranilic acid) or diaroyltartaric acids (e.g. dibenzoyltartaric acid).

According to the above processes, the desired compounds [I] may be obtained in the form of free base or salt or hydrate or alkanolate depending on the kinds of the starting materials and the reaction conditions. When they are obtained in the form of free base, they may be converted into their pharmaceutically acceptable salts of various inorganic or organic acids. Suitable acids include inorganic acids (e.g. hydrochoric acid, hydrobromic acid, hydroiodic acid, sulfuric acid, or phosphoric acid) and organic acids (e.g. citric acid, maleic acid, fumaric acid, tartaric acid, dibenzoyltartaric acid, acetic acid, benzoic acid, lactic acid, methanesulfonic acid, 2-naphthalenesulfonic acid, salicylic acid, or acetylaalicylic acid).

The preparation of the present compounds [I] and their pharmaceutically acceptable salts and further the compositions thereof are illustrated by the following Examples but are not limited thereto. In the Examples, percentages are by weight unless otherwise specified.

EXAMPLE 1 dl-1-Cyclohexyl-4-[2-(3-hydroxyphenyl)-1-phenylethyl]piperazine

In ethanol (60 ml) are dissolved 2-(3-hydroxyphenyl)-1-phenylethylamine (3.0 g) and N,N-bis(2-chloroethyl)-cyclohexylamine hydrochloride (2.6 g) and thereto is added sodium hydrogen carbonate (2.8 g). The mixture is refuxed with stirring for 24 hours. After the reaction, the solvent is distilled off under reduced pressure. To the residue is added a 10% hydrochloric acid (20 ml) and the mixture is allowed to cool. The resulting precipitates are colleced by filtration, washed with a small amount of cold water and then with acetone, and recrystallized from methanol to give the desired compound as dihydrochloride (2.6 g), melting point: 264°-270° C. (decomp.).

To the dihydrochloride thus obtained is added diluted potassium carbonate aqueous solution and the alkaline solution is extracted with ether. The extract is concentrated and the residue is recrystallized from benzene to give the free base a colorless needles, melting point: 140°-141° C.

The free base obtained above is dissolved in a small amount of methanol and the solution is made acidic with a 25% hydrobromic acid-acetic acid solution. The resultng precipitates are recrystallized from methanol to give dihydrobromide of the desired compound, meltng point: 268°-270° C.

EXAMPLE 2 l-1-Cyclohexyl-4-[2-(3-hydroxyphenyl)-1-phenylethyl]-piperazine

In ethanol (30 ml) are dissolved l-2-(3-hydroxyphenyl)-1-phenylethylamine (1.2 g) and N,N-bis(2- chloroethyl)cyclohexylamine hydrochloride (1.3 g) and thereto is added sodium hyrogen carbonate (1.4 g). The mixture is refluxed with stirring for 18 hours After the reaction, the solvent is distilled off under reduced pressure. To the residue is added a diluted potassium carbonate aqueous solution and the mixture is extracted with ethyl acetate. The ethyl acetate layer is washed with water, dried over anhydrous sodium sulfate and then the solvent is distilled off. The residue (free base) is treated with methanolic hydrochloric acid to give dihydrochloride, which is recrystallized from methanol to give the desired compound as dihydrochloride (0.9 g), colorless needles, melting point: 275°–280° C. (decom.). $[\alpha]_D^{29} = -48.8°$ (c=0.5, methanol)

EXAMPLE 3 d-1-Cyclohexyl-4-[2-(3-hydroxyphenyl)-1-phenylethyl]-piperazine

The above Example 2 is repeated excepting that d-2-(3-hydroxyphenyl)-1-phenylethylamine (1.1 g), N,N-bis(2-chloroethyl)cyclohexylamine hydrochloride (1.3 g) and sodium hydrogen carbonate (1.4 g) are used to give the desired compound as dihydrochloride (0.8 g), colorless needles, melting point: 275°–280° C. (decomp.). $[\alpha]_D^{30} = +48.6°$ (c=0.5, methanol)

EXAMPLE 4 l-1-Cyclohexyl-4-[2-(2-hydroxyphenyl)-1-phenylethyl]-piperazine

In ethanol (30 ml) are dissolved l-2-(2-hydroxyphenyl)-1-phenylethylamine (1.2 g) and N,N-bis(2-chloroethyl)-cyclohexylamine hydrochloride (1.3 g) and thereto is added sodium hydrogen carbonate (1.4 g). The mixture is refluxed with stirring for 20 hours. After the reaction, the solvent is distilled off under reduced pressure. To the residue is added a diluted potassium carbonate aqueous solution and the solution is extracted with ethyl acetate. The ethyl acetate layer is washed with water, dried over anhydrous sodium sulfate, and the solvent is distilled off. The residue (free base) is treated with methanolic hydrochloric acid to give dihydrochloride, which is recrystallized from methanol to give the desired compound as dihydrochloride (0.8 g), melting point: 248°–250° C. $[\alpha]_D^{28} = -93.0°$ (c=1.0, methanol)

EXAMPLE 5 l-1-Cyclohexyl-4-[1-phenyl-2-(3-tolyl)ethyl]piperazine

In ethanol (60 ml) are dissolved l-1-phenyl-2-(3-tolyl)ethylamine (2.3 g) and N,N-bis(2-chloroethyl)cyclohexylamine hydrochloride (2.6 g) and thereto is added sodium hydrogen carbonate (2.8 g). The mixture is refluxed with stirring for 20 hours. After the reaction, the solvent is distilled off under reduced pressure. To the residue is added a diluted sodium carbonate aqueous solution and the mixture is extracted with ether. The ether layer is washed with water, dried over anhydrous sodium sulfate, and the solvent is distilled off. The residue (free base) is treated wth methanolic hydrochloric acid to give dihydrochloride, which is recrystallized from methanol to give the desired compound as dihydrochloride (2.5 g), melting point: 249°–252° C. $[\alpha]_D^{29} = -55.8°$ (c=1.0, methanol)

EXAMPLE 6

1-1-(2-Methoxyphenyl)-4-[1-phenyl-2-(3-tolyl)ethyl]-piperazine

In ethanol (60 ml) are dissolved 1-1-phenyl-2-(3-tolyl)ethylamine (2.1 g) and N,N-bis(2-chloroethyl)-o-anisidine hydrochloride (2.8 g) and thereto is added sodium hydrogen carbonate (2.7 g). The mixture is refluxed with stirring for 24 hours. After the reaction, the solvent is distilled off under reduced pressure. To the residue is added a concentrated aqueous ammonia and the mixture is extracted with ether. The ether layer is dried over anhydrous sodium sulfate and the solvent is distilled off. The residue is treated with ethanolic hydrochloric acid to give hydrochloride, which is recrystallized from ethanol to give the desired compound as dihydrochloride hemihydrate (2.6 g), melting point: 231°–236° C., mass spectrum: m/e 386 (M+), $[\alpha]_D^{28} = -47.8°$ (c=1.0, methanol).

EXAMPLE 7 dl-1-(2-methoxyphenyl)-4-[2-(3-methoxyphenyl)-1-phenylethyl]piperazine

In dimethylformamide (40 ml) are dissolved dl-2-(3-methoxyphenyl)-1-phenylethylamine (2,3g) and N,N-bis(2-chloroethyl)-o-anisidine hydrochloride (2.8 g) and thereto is added sodium hydrogen carbonate (2.7 g). The mixture is refluxed with stirring for 10 hours. After cooling, the inorganic materials are filtered off from the reaction mixture. The solvent is distilled off from the filtrate. To the residue is added a concentrated aqueous ammonia and the mixture is extracted with ether. The ether layer is dried over anhydrous sodium sulfate and the solvent is distilled off. The residue is treated with ethanolic hydrochloric acid to give hydrochloride, which is recrystallized from ethanol to give the desired compound as dihydrochloride hemihydrate (2,2g), melting point: 225°–228° C.

The free base thereof has a melting point of 97°–99° C., which is recrystallized from ethanol.

EXAMPLE 8 l-1-Cyclohexyl-4-[2-(3-methoxyphenyl)-1-phenylethyl]piperazine

The above Example 2 is repeated excepting that l-2-(3-methoxyphenyl)-1-phenylethylamine (1.2 g), N,N-bis-(2-chloroethyl)cyclohexylamine hydrochloride (1.3 g) and sodium hydrogen carbonate (1.4 g) are used to give the desired compound as dihydrochloride (1.2 g), which is recrystallized from methanol, colorless needles, melting point: 243°–247° C., $[\alpha]_D^{29} = 47.8°$ (c=1.00, methanol).

EXAMPLE 9

1-1-(3-Methyl-2-butenyl)-4-([2-(3-hydroxyphenyl)-1-phenylethyl]piperazine

In ethanol (30 ml) are dissolved 1-2-(3-hydroxyphenyl)-1-phenylethylamine (1.3 g) and N,N-bis(2-chloroethyl)-3-methyl-2-butenylamine hydrochloride (1.2 g) and thereto is added sodium hydrogen carbonate (1.4 g). The mixture is refluxed with stirring for 18 hours. After the reaction, the solvent is distilled off under reduced pressure. To the residue is added a diluted potassium carbonate aqueous solution and the mixture is extracted with ethyl acetate. The ethyl acetate layer is washed with water, dried over anhydrous sodium sulfate, and the solvent is distilled off. The residue (free base) is treated with ethanolic hydrochloric acid to give dihydrochloride, which is recrystallized from ethanol to give the desired compound as dihydrochloride (1.1 g), melting point: 221°–224° C., $[\alpha]_D^{28} = -56.2°$ (c=1.00 methanol).

EXAMPLE 10

The following compounds are prepared in the same manner as described in the above Examples.

dl-1-Cyclohexyl-4-[2-(3-methoxyphenyl)-1-phenylethyl]-piperazine dihydrochloride, melting point: 240°–243° C.

dl-1-Cycloheptyl-4-[2-(3-methoxyphenyl)-1-phenylethyl]piperazine dihydrochloride, melting point: 230°–233° C.

dl-1-Cyclooctyl-4-[2-(3-methoxyphenyl)-1-phenylethyl]piperazine dihydrochloride, melting point: 213°–216° C.

dl-1-Cycloheptyl-4-[2-(3-hydroxyphenyl)-1-phenylethyl]piperazine dihydrobromide, melting point: 279°–281° C.

dl-1-Cyclooctyl-4-[2-(3-hydroxyphenyl)-1-phenylethyl]-piperazine dihydrobromide, melting point: 274°–276° C.

dl-1-Cyclohexyl-4-[1-phenyl-2-(2-methoxyphenyl)ethyl]-piperazine dihydrochloride, melting point: 236°–239° C.

dl-1-Cyclohexyl-4-[1-phenyl-2-(2-hydroxyphenyl)ethyl]-piperazine (free base), melting point: 185°–186° C.

l-1-Cyclohexyl-4-[2-(2-methoxyphenyl)-1-phenylethyl]-piperazine dihydrochloride hemihydrate, melting point: 248°–251° C.

l-1-(2-Methoxyphenyl)-4-[2-(3-methoxyphenyl)-1-phenylethyl]piperazine dihydrochloride hemihydrate, melting point: 229°–234° C.

dl-1-(2-Methoxyphenyl)-4-[2-(3-ethoxyphenyl)-1-phenylethyl]piperazine dihydrochloride hemihydrate, melting point: 218°–221° C.

dl-1-Cyclopentyl-4-[2-(3-hydroxyphenyl)-1-phenylethyl]piperazine dihydrobromide monohydrate, melting point: 242°–244° C.

dl-1-Cyclopentyl-4-[2-(3-methoxyphenyl)-1-phenylethyl]piperazine dihydrochloride hemihydrate, melting point: 222°–225° C.

dl-1-(3-Methyl-3-butenyl)-4-[2-(3-methoxyphenyl)-1-phenylethyl]piperazine dihydrochloride hemihydrate, melting point: 212°–215° C.

dl-1-(3-Methyl-2-butenyl)-4[2-(3-methoxyphenyl)-1-phenylethyl]piperazine dihydrochloride, melting point: 205°–209° C.

d-1-Cyclohexyl-4-[1-phenyl-2-(3-tolyl)ethyl]piperazine dihydrochloride, melting point: 249°–252° C.

dl-1-Cycloheptyl-4-[1-phenyl-2-(3-tolyl)ethyl]-piperazine dihydrochloride, melting point: 224°–227° C.

dl-1-Cyclohexyl-4-[1-phenyl-2-(3-tolyl)ethyl]piperazine dihydrochloride, melting point: 244°–247° C.

dl-1-(2-Methoxyphenyl)-4-[1-phenyl-2-(3-tolyl)ethyl]-piperazine dihydrochloride hemihydrate, melting point: 229°–232° C.

dl-1-Cyclooctyl-4-[1-phenyl-2-(3-tolyl)ethyl]piperazine dihydrochloride, melting point: 238°–240° C.

dl-1-(2-Methoxyphenyl)-4-[2-(3-hydroxyphenyl)-1-phenylethyl]piperazine dihydrochloride hemihydrate, melting point: 185°–188° C.

d-1-(2-Methoxyphenyl)-4-[2-(3-hydroxyphenyl)-1-phenyl ethyl]piperazine dihydrochloride hemihydrate, melting point: 181°–184° C.

dl-1-(3-Methyl-2-butenyl)-4-[2-(3-hydroxyphenyl)-1-phenylethyl]piperazine dihydrochloride monohydrate, melting point: 222°–224° C.

d-1-(3-Methyl-2-butenyl)-4-[2-(3-hydroxyphenyl)-1-phenylethyl]piperazine dihydrochloride, melting point: 221°–224° C.

dl-1-(3-Methyl-3-butenyl)-4-[2-(3-hydroxyphenyl)-1-phenylethyl]piperazine dihydrochloride hemihydrate, melting point: 209°–212° C.

l-1-(3-Methyl-2-butenyl)-4-[2-(3-methoxyphenyl)-1-phenylethyl]piperazine dihydrochloride, melting point: 215°–217° C.

dl-1-(2-Hydroxyphenyl)-4-[2-(3-hydroxyphenyl)-1-phenylethyl]piperazine dihydrobromide, melting point: 219°–224° C.

dl-1-(3-Methoxyphenyl)-4-[2-(3-hydroxyphenyl)-1-phenylethyl]piperazine dihydrochloride, melting point: 190°–195° C.

dl-1-(3-Hydroxyphenyl)-4-[2-(3-hydroxyphenyl)-1-phenylethyl]piperazine dihydrochloride, melting point: 196°–203° C.

l-1-(4-Methoxyphenyl)-4-[2-(3-hydroxyphenyl)-1-phenylethyl]piperazine dihydrochloride, melting point: 193°–198° C.

dl-1-(4-Methoxyphenyl)-4-[2-(3-hydroxyphenyl)-1-phenylethyl]piperazine dihydrochloride, melting point: 187°–191° C.

dl-1-(2-Chlorophenyl)-4-[2-(3-hydroxyphenyl)-1-phenylethyl]piperazine dihydrochloride hemihydrate, melting point: 202°–205° C.

l-1-Allyl-4-[2-(3-hydroxyphenyl)-1-phenylethyl]-piperazine dihydrochloride monoethanolate, melting point: 197°–204° C.

dl-1-Propyl-4-[2-(3-hydroxyphenyl)-1-phenylethyl]-piperazine dihydrochloride hemihydrate, melting point: 212°–214° C.

EXAMPLE 11 dl-1-Cyclohexyl-4-[1-phenyl-2-(2-hydroxyphenyl)-ethyl]piperazine

In ethanol (30 ml) are dissolved N,N-bis(2-chloroethyl)-1-phenyl-2-(2-hydroxyphenyl)ethylamine hydrochloride (1.9 g) and cyclohexylamine (0.7 g) and thereto is added sodium hydrogen carbonate (1.4 g). The mixture is refluxed with stirring for 24 hours. After the reaction, the solvent is distilled off. To the residue is added a diluted aqueous ammonia and the alkaline solution is extracted with chloroform. The chloroform layer is washed with water, dried over anhydrous sodium sulfate, and the solvent is distilled off. The crystalline residue (crude free base) is dissolved in a small amount of ethanol and there to is added a 25% hydrobromic acid-acetic acid solution and the mixture is allowed to cool. The precipitated crystals are recrystallized from ethanol to give the desired compound as dihydrobromide (1.4 g), melting point: 245.5°–247.5° C.

To the dihydrobromide obtained above is added a diluted sodium carbonate aqueous solution and the alkaline solution is extracted with ether. The free base isolated from the ether extract is recrystallized from methanol to give the free base of the desired compound, melting point: 185°–186° C.

The free base obtained above is treated with ethanolic hydrochloric acid and the resulting crystals are recrystallized from ethanol to give to the dihydrochloride of the desired compound, melting point: 225°–227° C.

EXAMPLE 12 dl-1-(2-Methoxyphenyl)-4-[2-(3-methoxyphenyl)-1-phenylethyl]piperazine

In dimethylformamide (50 ml) is dissolved dl-N,N-bis(2-chloroethyl)-2-(3-methoxyphenyl)-1-phenylethylamine hydrochloride (5.6 g) and thereto is added o-anisidine (7.3 g). The mixture is refluxed with stirring for 5 hours. After the reaction, the solvent is distilled off under reduced pressure. To the residue is added a concentrated aqueous ammonia and the alkaline solution is extracted with ether. The ether layer is washed with water, dried over anhydrous sodium sulfate, and the solvent is distilled off. The oily residue is distilled under reduced pressure to remove excess of o-anisidine. The distillation residue is dissolved in ethanol and treated with ethanolic hydrochloric acid to give the hydrochloride, which is recrystallized from ethanol to give the desired compound as dihydrochloride hemihydrate (2.8 g), melting point: 225°–228° C.

EXAMPLE 13 dl-1-(2-Methoxyphenyl)-4-[1-phenyl-2-(3-tolyl)ethyl]-piperazine

In dimethylformamide (20 ml) is dissolved dl-N,N-bis(2-chloroethyl)-1-phenyl-2-(3-tolyl)ethylamine hydrochloride (5.5 g) and thereto is added o-anisidine (7.5 g). The mixture is refluxed with stirring for 5 hours. After the reaction, the solvent is distilled off under reduced pressure. To the residue is added a concentrated aqueous ammonia and the mixture is extracted with ether. The ether layer is dried over anhydrous sodium sulfate and the solvent is distilled off. The oily residue is distilled under reduced pressure to remove excess of o-anisidine. The residue is treated with ethanolic hydrochloric acid to give the hydrochloride, which is recrystallized from ethanol to give the desired compound as dihydrochloride hemihydrate (5.5 g), melting point: 229°–232° C.

EXAMPLE 14 dl-1-(2-Methoxyphenyl)-4-[2-(3-hydroxyphenyl)-1-phenylethyl]piperazine

In dimethylformamide (70 ml) is dissolved dl-N,N-bis(2-bromoethyl)-2-(3-hydroxyphenyl)-1-phenylethylamine hydrobromide (5.1 g) and thereto is added o-anisidine (6.5 g). The mixture is refluxed with stirring for 5 hours. After the reaction, the solvent is distilled off under reduced pressure. To the residue is added a concentrated aqueous ammonia and the alkaline mixture is extracted with ether. The ether layer is washed with water, dried over anhydrous sodium sulfate, and the solvent is distilled off. The oily residue is distilled under reduced pressure to remove excess of o-anisidine. The crystalline distillation residue (free base) is dissolved in ethanol and treated with methanolic hydrochloric acid to give the hydrochloride, which is recrystallized from methanol to give the desired compound as dihydrochloride hemihydrate (2.8 g), melting point: 185°–188° C.

EXAMPLE 15 dl-1-Cyclohexyl-4-[2-(3-hydroxyphenyl)-1-phenylethyl]-piperazine

In ethanol (60 ml) are dissolved dl-N,N-bis(2-chloroethyl)-1-phenyl-2-(3-hydroxyphenyl)ethylamine hydrochloride (3.7 g) and cyclohexylamine (1.4 g) and thereto is added sodium hydrogen carbonate (3.0 g). The mixture is refluxed with stirring for 24 hours. After the reaction, the solvent is distilled off. To the residue is added a diluted sodium carbonate aqueous solution and the mixture is extracted with ethyl acetate. The ethyl acetate layer is washed with water, dried over anhydrous sodium sulfate, and the solvent is distilled off. The residue (crude free base) is dissolved in a small amount of methanol and the mixture is made acidic with a 25% hydrobromic acid-acetic acid solution and allowed to cool. The precipitated crystals are washed with a mixture of acetone and ether and recrystallized from methanol to give the desired compound as dihydrobromide (2.9 g), melting point: 268°–270° C.

The dihydrobromide obtained above is treated with a diluted potassium carbonate aqueous solution in a conventional manner and the obtained crystals are recrystallized from benzene to give the free base of the desired compound, colorless needles, melting point: 140°–141° C.

The free base thus obtained is treated with methanolic hydrochloric acid and the obtained crystals are recrystallized from methanol to give the dihydrochloride of the desired compound, melting point: 264°–270° C. (decomp.).

EXAMPLE 16

The following compounds are prepared in the same manner as described above Examples 11 to 15.

dl-1-Cycloheptyl-4-[2-(3-hydroxyphenyl)-1-phenylethyl]piperazine dihydrobromide, melting point: 279°–281° C.

dl-1-Cyclooctyl-4-[2-(3-hydroxyphenyl)-1-phenylethyl]-piperazine dihydrobromide, melting point: 274°–276° C.

l-1-Cyclohexyl-4-[2-(3-hydroxyphenyl)-1-phenylethyl]-piperazine dihydrochloride, melting point: 275°–280° C. (decomp.).

d-1-Cyclohexyl-4-[2-(3-hydroxyphenyl)-1-phenylethyl]-piperazine dihydrochloride, melting point: 275°–280° C. (decomp.).

dl-1-Cyclohexyl-4-[1-phenyl-2-(3-tolyl)ethyl]piperazine dihydrochloride, melting point: 244°–247° C.

dl-1-(3-Methyl-2-butenyl)-4-[2-(3-methoxyphenyl)-1-phenylethyl]piperazine dihydrochloride, melting point: 205°–209° C.

dl-1-(3-Methyl-3-butenyl)-4-[2-(3-hydroxyphenyl)-1-phenylethyl]piperazine dihydrochloride hemihydrate, melting point: 209°–212° C.

dl-1-(3-Methyl-2-butenyl)-4-[2-(3-hydroxyphenyl)-1-phenylethyl]piperazine dihydrochloride monohydrate, melting point: 222°–224° C.

dl-1-(3-Hydroxyisoamyl)-4-[2-(3-hydroxyphenyl)-1-phenylethyl]piperazine dihydrochloride sesquihydrate, melting point: 200°–202° C.

dl-1-(4-Methoxyphenyl)-4-[2-(3-hydroxyphenyl)-1-phenylethyl]piperazine dihydrochloride, melting point: 187°–191° C.

dl-1-Allyl-4-[2-(3-hydroxyphenyl)-1-phenylethyl]-piperazine dihydrochloride monoethanolate, melting point: 194°–197° C.

l-1-(3-Methyl-2-butenyl)-4-[2-(3-hydroxyphenyl)-1-phenylethyl]piperazine dihydrochloride, melting point: 221°–224° C.

l-1-Cyclohexyl-4-[1-phenyl-2-(3-tolyl)ethyl]piperazine dihydrochloride, melting point: 249°–252° C.

l-1-(3-Methyl-2-butenyl)-4-[2-(3-methoxyphenyl)-1-phenylethyl]piperazine dihydrochloride, melting point: 215°–217° C.

l-1-(2-Methoxyphenyl)-4-[1-phenyl-2-(3-tolyl)ethyl]-piperazine dihydrochloride hemihydrate, melting point: 231°–236° C.

l-1-Cyclohexyl-4-[2-(2-hydroxyphenyl)-1-phenylethyl]-piperazine dihydrochloride, melting point: 248°–250° C.

1-1-(2-Methoxyphenyl)-4-[2-(3-methoxyphenyl)-1-phenylethyl]piperazine dihydrochloride hemihydrate, melting point: 229°–234° C.

EXAMPLE 17 dl-1-(3-Methyl-2-butenyl)-4-[2-(3-hydroxyphenyl)-1-phenylethyl]piperazine

In dimethylsulfoxide (150 ml) are dissolved dl-N-[2-(3-hydroxyphenyl)-1-phenylethyl]piperazine (8.9 g) and 1-bromo-3-methyl-2-butene (5.2 g) and thereto is added sodium hydrogen carbonate (4.3 g). The mixture is heated with stirring at 85°–95° C. for 15 hours. After the reaction, the solvent is distilled off under reduced pressure. To the residue is added a diluted sodium carbonate aqueous solution and the mixture is extracted with ethyl acetate. The organic layer is washed with water, dried over anhydrous sodium sulfate, and the solvent is distilled off. The oily residue is dissolved in benzene and the solution is subjected to a silica gel column chromatography. The eluates with a 33% (V/V) acetone-benzene solution are collected and treated with ethanolic hydrochloric acid to give the dihydrochloride, which is recrystallized from ethanol to give the desired compound as dihydrochloride monohydrate (6.9 g), melting point: 222°–224° C., mass spectrum: m/e 350 (M+).

EXAMPLE 18 dl-1-(3-Methyl-2-butenyl)-4-[2-(3-methoxyphenyl)-1-phenylethyl]piperazine

In dimethylformamide (70 ml) are dissolved dl-N-[2-(3-methoxyphenyl)-1-phenylethyl]piperazine (14.0 g) and 1-bromo-3-methyl-2-butene (8.4 g) and thereto is added sodium hydrogen carbonate (6.6 g). The mixture is heated with stirring at 100°–110° C. for 10 hours. After the reaction, the solvent is distilled off under reduced pressure. To the residue is added water and the mixture is extracted with ether. The ether layer is washed with water, dried over anhydrous sodium sulfate, and the solvent is distilled off. The residue is dissolved in chloroform and the mixture is subjected to a silica gel column chromatography. The eluates with a 2% (V/V) methanol-chloroform solution are collected and the solvent is distilled off therefrom. The residue is treated with ethanolic hydrochloric acid to give the hydrochloride, which is recrystallized from ethanol to give the desired compound as dihydrochloride (13.5 g), melting point: 205°–209° C.

EXAMPLE 19

The following compounds are prepared in the same manner as described in the above Examples 17 and 18.

dl-1-(3-Methyl-3-butenyl)-4-[2-(3-hydroxyphenyl)-1-phenylethyl]piperazine dihydrochloride hemihydrate, melting point: 209°–212° C.

dl-1-Allyl-4-[2-(3-hydroxyphenyl)-1-phenylethyl]piperazine dihydrochloride monoethanolate, melting point: 194°–197° C.

l-1-(3-Methyl-2-butenyl)-4-[2-(3-hydroxyphenyl)-1-phenylethyl]piperazine dihydrochloride, melting point: 221°–224° C.

l-1-(3-Methyl-2-butenyl)-4-[2-(3-methoxyphenyl)-1-phenylethyl]piperazine dihydrochloride, melting point: 215°–217° C.

EXAMPLE 20 dl-1-(3-Methyl-2-butenyl)-4-[2-(3-hydroxyphenyl)-1-phenylethyl]piperazine

In tetrahydrofuran (150 ml) is dissolved dl-1-(3-methylcrotonyl)-4-[2-(3-hydroxyphenyl)-1-phenylethyl]piperazine (4.1 g). The solution is added dropwise to a suspension of lithium aluminum hydride (2.2 g) in tetrahydrofuran (100 ml). The mixture is refluxed for 10 hours. After cooling, water is added to the reaction mixture and the inorganic materials are filtered off therefrom. The filtrate is distilled under reduced pressure to remove the solvent. The residue is dissolved in ethyl acetate, and the mixture is dried over anhydrous sodium sulfate and the solvent is distilled off. The oily residue (crude free base) is dissolved in benzene and the mixture is subjected to a silica gel column chromatography. The eluates with a 33% (V/V) acetone-benzene solution are collected and treated with ethanolic hydrochloric acid to give the dihydrochloride, which is recrystallized from ethanol to give the desired compound as dihydrochloride monohydrate (2.0 g), melting point: 222°–224° C., mass spectrum: m/e 350 (M+).

EXAMPLE 21

The following compounds are prepared in the same manner as described in Example 20.

dl-1-(3-Methyl-2-butenyl)-4-[2-3-methoxyphenyl)-1-phenylethyl]piperazine dihydrochloride, melting point: 205°–209° C.

l-1-(3-Methyl-2-butenyl)-4-[2-(3-hydroxyphenyl)-1-phenylethyl]piperazine dihydrochloride, melting point: 221°–224° C.

l-1-(3-Methyl-2-butenyl)-4-[2-(3-methoxyphenyl)-1-phenylethyl]piperazine dihydrochloride, melting point: 215°–217° C.

dl-1-(3-Methyl-3-butenyl)-4-[2-(3-hydroxyphenyl)-1-phenylethyl]piperazine dihydrochloride hemihydrate, melting point: 209°–212° C.

EXAMPLE 22 dl-1-Cyclohexyl-4-[1-phenyl-2-(2-hydroxyphenyl)ethyl]piperazine

A mixture of dl-1-cyclohexyl-4-[1-phenyl-2-(2-methoxyphenyl)ethyl]piperazine dihydrochloride (12.2 g), 48% hydrobromic acid (115 ml) and glacial acetic acid (60 ml) is refluxed for 4 hours. After the reaction, the reaction mixture is made alkaline with aqueous ammonia and the mixture is extracted with chloroform. The chloroform layer is dried over anhydrous sodium sulfate and the solvent is distilled off. The residue is dissolved in ethanol and the mixture is treated with a 25% hydrobromic acid-acetic acid solution to give the dihydrobromide, which is recrystallized from ethanol to give the desired compound as dihydrobromide (9.5 g), melting point: 245°–247.5° C.

EXAMPLE 23 dl-1-Cyclohexyl-4-[2-(3-hydroxyphenyl)-1-phenylethyl]-piperazine (i) A mixture of dl-1-cyclohexyl-4-[2-(3-methoxyphenyl)-1-phenylethyl]piperazine dihydrochloride (3.3 g), 47% hydrobromic acid (33 ml) and glacial acetic acid (16 ml) is refluxed for 5 hours. The reaction mixture is allowed to cool and the precipitated crystals are collected by filtration, washed with acetone and recrystallized from methanol to give the desired compound as dihydrobromide (2.9 g), melting point: 268°–270° C.

The free base of the desired compound is prepared by treating the dihydrobromide obtained above with an alkali and recrystallizing the resulting crystals from benzene, melting point: 140°–141° C.

(ii) A mixture of dl-1-cyclohexyl-4-[2-(3-methoxyphenyl)-1-phenylethyl]piperazine dihydrochloride (1.5 g) and anhydrous aluminum chloride (4.0 g) is kneaded well at moisture-free atmosphere, and the resultant is heated with stirring under nitrogen gas at 110°–125° C. for about 15 minutes. After cooling, ice is added to the reaction mixture and the insoluble materials are taken out by filtration and washed with a small amount of a cold, diluted hydrochloric acid and then with acetone and ether. The materials are dissolved in water and the mixture is made alkaline with sodium carbonate and extracted with ethyl acetate. The ethyl acetate layer is washed with water, dried over anhydrous sodium sulfate, and the solvent is distilled off. The residue is treated with methanolic hydrochloric acid and recrystallized from methanol to give the desired compound as dihydrochloride (0.9 g), melting point: 264°–270° C. (decomp.).

EXAMPLE 24 l-1-Cyclohexyl-4-[2-(3-hydroxyphenyl)-1-phenylethyl]-piperazine

A mixture of l-1-cyclohexyl-4-[2-(3-methoxyphenyl)-1-phenylethyl]piperazine dihydrochloride (0.45 g), 47% hydrobromic acid (4.5 ml) and acetic acid (1.5 ml) is refluxed for 0.5 hour. After the reaction, the solvent is distilled off under reduced pressure. To the residue is added a 10% sodium carbonate aqueous solution and the alkaline mixture is extracted with chloroform. The chloroform layer is dried over anhydrous sodium sulfate, and the solvent is distilled off. The residue is treated with ethanolic hydrochloric acid and recrystallized from methanol to give the desired compound as dihydrochloride (0.3 g), melting point: 275°–280° C. (decomp.), $[\alpha]_D^{29} = -49.1°$ (c=0.50, methanol).

EXAMPLE 25

The following compounds are prepared in the same manner as described in the above Examples 22 to 24.

d-1-Cyclohexyl-4-[2-(3-hydroxyphenyl)-1-phenylethyl]-piperazine dihydrochloride, melting point: 275°–280° C. (decomp.)

dl-1-Cycloheptyl-4-[2-(3-hydroxyphenyl)-1-phenylethyl]piperazine dihydrobromide, melting point: 279°–281° C.

dl-1-Cyclooctyl-4-[2-(3-hydroxyphenyl)-1-phenylethyl]-piperazine dihydrobromide, melting point: 274°–276° C.

dl-1-(3-Methyl-2-butenyl)-4-[2-(3-hydroxyphenyl)-1-phenylethyl]piperazine dihydrochloride monohydrate, melting point: 222°–224° C.

dl-1-(3-Methyl-3-butenyl)-4-[2-(3-hydroxyphenyl)-1-phenylethyl]piperazine dihydrochloride hemihydrate, melting point: 209°–212° C.

l-1-(3-Methyl-2-butenyl)-4-[2-(3-hydroxyphenyl)-1-phenylethyl]piperazine dihydrochloride, melting point: 221°–224° C.

l-1-Cyclohexyl-4-[2-(2-hydroxyphenyl)-1-phenylethyl]-piperazine dihydrochloride, melting point: 248°–250° C.

EXAMPLE 26 dl-1-Cyclohexyl-4-[1-phenyl-2-(2-hydroxyphenyl)ethyl]-piperazine

In a 50% ethanol-acetic acid solution (50 ml) is dissolved dl-1-cyclohexyl-4-[2-(2-benzyloxyphenyl)-1-phenylethyl]piperazine dihydrochloride (0.5 g) and thereto is added a 10% palladium-carbon (0.4 g) and the mixture is subjected to a catalytic reduction. When about one equimolar amount of hydrogen is absorbed, the reaction is stopped and the catalyst is filtered off. The filtrate is distilled to remove the solvent. The crystalline residue is recrystallized from ethanol to give the desired compound as dihydrochloride (0.3 g), melting point: 225°–227° C.

EXAMPLE 27 dl-1-Cyclohexyl-4-[2-(3-hydroxyphenyl)-1-phenylethyl]piperazine

In a 50% ethanol-acetic acid solution (50 ml) is dissolved dl-1-cyclohexyl-4-[2-(3-benzyloxyphenyl)-1-phenylethyl]piperazine dihydrochloride (0.5 g) and thereto is added a 10% palladium-carbon (0.4 g) and the mixture is subjected to a catalytic reduction. When about one equimolar amount of hydrogen is absorbed, the reaction is stopped and the catalyst is filtered off. The filtrate is distilled to remove the solvent. The crystalline residue is recrystallized from methanol to give the desired compound as dihydrochloride (0.3 g), melting point: 264°–270° C. (decomp.)

EXAMPLE 28

The following compounds are prepared in the same manner as described in the above Examples 26 and 27.

l-1-Cyclohexyl-4-[2-(3-hydroxyphenyl)-1-phenylethyl]-piperazine dihydrochloride, melting point: 275°–280° C. (decomp.)

l-1-Cyclohexyl-4-[2-(2-hydroxyphenyl)-1-phenylethyl]-piperazine dihydrochloride, melting point: 248°–250° C.

dl-1-(2-Methoxyphenyl)-4-[2-(3-hydroxyphenyl)-1-phenylethyl]piperazine dihydrochloride hemihydrate, melting point: 185°–188° C.

dl-1-(4-Methoxyphenyl)-4-[2-(3-hydroxyphenyl)-1-phenylethyl]piperazine dihydrochloride, melting point: 187°–191° C.

EXAMPLE 29 dl-1-Cyclohexyl-4-[1-phenyl-2-(2-hydroxyphenyl)ethyl] piperazine

A mixture of dl-1-cyclohexyl-4-[2-(2-propionyloxyphenyl)-1-phenylethyl]piperazine dihydrochloride (0.5 g), 10% hydrochloric acid (20 ml) and ethanol (10 ml) is refluxed for one hour. After the reaction, the solvent is distilled off. The residue is dried and recrystallized from ethanol to give the desired compound as dihydrochloride (0.3 g), melting point: 225°–227° C.

EXAMPLE 30 dl-1-Cyclohexyl-4-[2-(3-hydroxyphenyl)-1-phenylethyl]-piperazine

A mixture of dl-1-cyclohexyl-4-[2-(3-propionyloxyphenyl)-1-phenylethyl]piperazine dihydrochloride (0.5 g), 10% hydrochloric acid (20 ml) and methanol (10 ml) is refluxed for 2 hours. After the reaction, the solvent is distilled off. The residue is dried and recrystallized from methanol to give the desired compound as dihydrochloride (0.35 g), melting point: 264°–270° C. (decomp.).

EXAMPLE 31

The following compounds are prepared in the same manner as described in the above Examples 29 and 30.

dl-1-(2-Methoxyphenyl)-4-[2-(3-hydroxyphenyl)-1-phenylethyl]piperazine dihydrochloride hemihydrate, melting point: 185°–188° C.

1-1-Cyclohexyl-4-[2-(3-hydroxyphenyl)-1-phenylethyl]-piperazine dihydrochloride, melting point: 275°–280° C. (decomp.).

1-1-Cyclohexyl-4-[2-(2-hydroxyphenyl)-1-phenylethyl]-piperazine dihydrochloride, melting point: 248°–250° C.

1-1-(3-Methyl-2-butenyl)-4-[2-(3-hydroxyphenyl)-1-phenylethyl]piperazine dihydrochloride, melting point: 221°–224° C.

dl-1-(4-Methoxyphenyl)-4-[2-(3-hydroxyphenyl)-1-phenylethyl]piperazine dihydrochloride, melting point: 187°–191° C.

EXAMPLE 32 dl-1-Cyclohexyl-4-[1-phenyl-2-(3-propionyloxyphenyl)ethyl]piperazine

A mixture of dl-1-cyclohexyl-4-[2-(3-hydroxyphenyl)-1-phenylethyl]piperazine dihydrochloride (5.2 g), propionic anhydride (10.0 g) and pyridine (100 ml) is refluxed for 4 hours. After the reaction, the solvent is distilled off under reduced pressure. To the residue is added acetone. The precipitated crystals are collected by filtration and recrystallized from ethanol to give the desired compound as dihydrochloride (4.5 g), melting point: 219°–222° C.

In the same manner as described above, the following compound is prepared.

dl-1-Cyclohexyl-4-[1-phenyl-2-(2-propionyloxyphenyl)ethyl]piperazine dihydrochloride, melting point: 222°–227° C.

EXAMPLE 33

Optical resolution of dl-1-cyclohexyl-4-[2-(3-hydroxyphenyl)-1-phenylethyl]piperazine To a warmed solution of dl-1-cyclohexyl-4-[2-(3-hydroxyphenyl)-1-phenylethyl]piperazine (13.6 g) in 95% ethanol (70 ml) is added a warmed solution of l-2'-nitrotartranilic acid (21.1 g) in 95% ethanol (70 ml). The mixture is allowed to cool. The precipitated crystals are separated by filtration and fractionally recrystallized from 95% ethanol to give l-1-cyclohexyl-4-[2-(3-hydroxyphenyl)-1-phenylethyl]-piperazine di-l-2'-nitrotartranilate (6.7 g), yellow prisms, melting point: 157°–158° C., $[\alpha]_D^{29} = -64.0°$ (c=2, methanol).

To the salt thus obtained is added water and the mixture is made alkaline with sodium carbonate and extracted with ethyl acetate. The ethyl acetate layer is washed with water, dried over anhydrous sodium sulfate, and the solvent is distilled off. The residue (free base) is treated with methanolic hydrochloric acid to give the dihydrochloride, which is recrystallized from methanol to give l-1-cyclohexyl-4-[2-(3-hydroxyphenyl)-1-phenylethyl]piperazine dihyrochloride, melting point: 275°–280° C. (decomp.), $[\alpha]_D^{29} = -49.1°$ (c=0.5, methanol).

Besides, the mother liquid obtained after the separation of the l-2'-nitrotartranilate in the above procedure is distilled to remove the solvent. To the residue is added a diluted sodium carbonate aqueous solution and the alkaline mixture is extracted with ethyl acetate. The ethyl acetate layer is washed with water, dried over anhydrous sodium sulfate, and the solvent is distilled off. The residue (crude free base, 6.0 g) is dissolved in 95% ethanol (30 ml) and thereto is added a warmed solution of d-2'-nitrotartranilic acid (9.3 g) in 95% ethanol (30 ml), and the mixture is allowed to cool. The precipitated crystals are separated by filtration and fractionally recrystallized from 95% ethanol to give d-1-cyclohexyl-4-[2-(3-hydroxyphenyl)-1-phenylethyl]-piperazine di-d-2'-nitrotartranilate (4.3 g), melting point: 157°–158° C. $[\alpha]_D^{32} = +63.8°$ (c=2, methanol).

The salt obtained above is treated with a diluted sodium carbonate aqueous solution and the resulting free base is treated with methanolic hydrocloric acid to give the dihydrochloride, which is recrystallized from methanol to give d-1-cyclohexyl-4-[2-(3-hydroxyphenyl)-1-phenylethyl]piperazine dihydrochloride, melting point: 275°–280° C. (decomp.). $[\alpha]_D^{29} = +49.0°$ (c=0.5, methanol).

EXAMPLE 34 l-1-Cyclohexyl-4-[2-(2-hydroxyphenyl)-1-phenylethyl]-piperazine.

To a warmed solution of dl-1-cyclohexyl-4]2-(2-hydroxyphenyl)-1-phenylethyl]piperazine (28.5 g) in 95% ethanol (190 ml) is added a warmed solution of l-2'-nitrotartranilic acid (43.0 g) in 95% ethanol (190 ml), and the mixture is allowed to cool. The precipiated crystals are separated by filtration and fractionally recrystallized from 95% ethanol to give l-1-cyclohexyl-4-[2-(2-hydroxyphenyl)-1-phenylethyl]piperazine di-l-2'-nitrotartranilate (sesquiethanolate) (18.0 g), melting point; 102°–105° C., $[\alpha]_D^{27} = -65.5°$ (c=2.0, methanol).

To the salt thus obtain is added water and the mixture is made alkaline with sodium carbonate and extracted with ethyl acetate. The ethyl acetate layer is washed with water, dried over anhydrous sodium sulfate, and the solvent is distilled off. The residue (free base) is treated with methanolic hydrochloric acid to give the dihydrochloride, which is recrystallized from methanol to give the desired compound as dihydrochloride, melting point: 248°–250° C., $[\alpha]_D^{28} = -93.0°$ (c=1.0, methanol).

In the same manner as described above, the following compound is prepared.

l-1-Cyclohexyl-4-[2-(2-methoxyphenyl)-1-phenylethyl]-piperazine dihyrochloride hemihydrate, melting point: 248°–251° C.

EXAMPLE 35 l-1-Cyclohexyl-4-[1-phenyl-2-(3-tolyl)ethyl]-piperazine.

A warmed mixture of dl-1-cyclohexyl-4-[1-phenyl-2-(3-tolyl)ethyl]piperazine (3.0 g), dibenzoyl-d-tartaric acid monohydrate (3.2 g) and ethanol (100 ml) is allowed to cool. The precipitated crystals are separated by filtration and fractionally recrystallized from 95% ethanol to give l-1-cyclohexyl-4-[1-phenyl-2-(3-tolyl)ethyl[piperazine dibenzoyl-d-tartarate sesquihydrate (1.2 g), melting point: 150°–151° C. (decomp.), $[\alpha_D^{28} = -83.0°$ (c=1.0, methanol).

To the salt thus obtained is added water and the mixture is made alkaline with sodium carbonate and extracted with ether. The ether layer is washed with water, dried over anhydrous sodium sulfate, and the solvent is distilled off. The crystalline residue (free base) is treated with methanolic hydrochloric acid to give the dihydrochloride, which is recrystallized from methanol to give the desired compound as dihydrochloride, melting point: 249°–252° C., $[\alpha]_D^{28} = -56.1°$ (c=1.0, methanol).

EXAMPLE 36 l-1-Cyclohexyl-4-[2-(3-methoxyphenyl)-1-phenylethyl]-piperazine

To a warmed solution of dl-1-cyclohexyl-4-[2-(3-methoxyphenyl)-1-phenylethyl]piperazine (16.9 g) in 95% ethanol (94ml) is added a warmed solution of l-2'-nitrotartranilic acid (24.2 g) in 95% ethanol (94 ml), and the mixture is allowed to cool. The precipitated crystals are separated by filtration and fractionally recrystallized from 95% ethanol to give di-l-2'-nitrotartranilic acid salt of the desired compound (9.0 g), melting point: 150°–151° C., $[\alpha]_D^{26} = -62.0°$ (c=2.00. methanol).

To the salt thus obtained is added water and the mixture is made alkaline with sodium carbonate and extracted with ethyl acetate. The ethyl acetate layer is washed with water, dried over anhydrous sodium sulfate, and the solvent is distilled off. The residue (free base) is treated with methanolic hydrochloric acid to give the dihydrochloride, which is recrystallized from methanol to give the desired compound as dihydrochloride, melting point: 243°–247° C., $[\alpha]_D^{29} = -47.8°$ (c=1.00, methanol).

EXAMPLE 37

Optical resolution of dl-1-(3-methyl-2-butenyl)-4-[2-(3-hydroxyphenyl)-1-phenylethyl]piperazine.

To a warmed solution of dl-1-(3-methyl-2-butenyl)-4-[2-(3-hydroxyphenyl)-1-phenylethyl]piperazine (10.2 g) in 95% ethanol (50 ml) is added a warmed solution of l-2'-nitrotartranilic acid (16.6 g) in 95% ethanol (50 ml), and the mixture is concentrated till 1/3 in volume and allowed to cool. The precipitated crystals are separated by filtration and fractionally recrystallized from ethanol to give l-1-(3-methyl-2-butenyl)-4-[2-(3-hydroxyphenyl)-1-phenylethyl]piperazine di-l-2'-nitrotartranilate (7.7 g), yellow needles, melting point: 126.5°–128° C., $[\alpha]_D^{30} = -64.4°$ (c=2.00, methanol).

To the salt thus obtained is added water and the mixture is made alkaline with sodium carbonate and extracted with ethyl acetate. The ethyl acetate layer is washed with water, dried over anhydrous sodium sulfate, and the solvent is distilled off. The residue (free base) is treated with ethanolic hydrochloric acid to give the dihydrochloride, which is recrystallized from ethanol to give l-1-(3-methyl-2-butenyl)-4-[2-(3-hydroxyphenyl)-1-phenylethyl]piperazine dihydrochloride, melting point: 221°–224° C., $[\alpha]D_D^{28} = -56.2°$ (c=1.00, methanol).

The mother liquid obtained after the separation of the l-2'-nitrotartranilate in the above procedure is distilled to remove the solvent. To the residue is added a diluted sodium carbonate aqueous solution and the alkaline solution is extracted with ethyl acetate. The ethyl acetate layer is washed with water, dried over anhydrous sodium sulfate, and the solvent is distilled off. The residue (crude free base) is dissolved in 95% ethanol (20 ml) and thereto is added a warmed solution of d-2'-nitrotartranilic acid (8.5 g) in 95 % ethanol (20 ml), and the mixture is concentrated till 1/3 in volume and allowed to cool. The precipitated crystals are separated by filtration and fractionally recrystallized from ethanol to give d-1-(3-methyl-2-butenyl)-4-[2-(3-hydroxyphenyl)-1phenylethyl]piperazine di-d-2'-nitrotartranilate (5.5 g), melting point: 126.5°–128° C., $[\alpha]_D^{29} = +64.7°$ (c=2.00, methanol).

The salt thus obtained is treated with a diluted sodium carbonate aqueous solution to give a free base, and the free base is treated with ethanolic hydrochloric acid to give the dihydrochloride, which is recrystallized from ethanol to give d-1-(3-methyl-2-butenyl)-4-[2-(3-hydroxyphenyl)-1-phenylethyl]piperazine dihydrochloride, melting point: 221°–224° C., $[\alpha]_D^{28} = +56.0°$ (c=1.00, methanol).

EXAMPLE 38 l-1-(2-Methoxyphenyl)-4-[1-phenyl-2-(3-tolyl)ethyl]-piperazine

To a warmed solution of dl-1-(2-methoxyphenyl)-4-[1-phenyl-2-(3-tolyl)ethyl]piperazine (31.0 g) in ethanol (150 ml) is added a warmed solution of l-2'-nitrotartranilic acid (22.0 g) in ethanol (150 ml.), and the mixture is allowed to stand at room temperature. The precipitated crystals are separated by filtration and fractionally recrystallized from ethanol to give l-1-(2-methoxyphenyl)-4-[1-phenyl-2-(3-tolyl)-ethyl]piperazine l-2'-nitrotartranilate hemidrate (11 g), melting point: 91°–93° C., $[\alpha]_D^{28} = -63.6°$ (c=2.0, methanol).

To the salt thus obtained is added water and the mixture is made alkaline with sodium carbonate and extracted with ethyl acetate. The ethyl acetate layer is washed with water, dried over anhydrous sodium sulfate, and the solvent is distilled off. The residue (free base) is treated with ethanolic hydrochloric acid to give the dihydrochloride, which is recrystallized from ethanol to give the desired compound as dihydrochloride hemihydrate, melting point: 231°–236° C., $[\alpha]_D^{28} = -47.8°$ (c=1.0, methanol), mass spectrum: m/e 386 (M+).

In the same manner as described above, the following compounds are prepared:

l-1-(2-Methoxyphenyl)-4-[1-phenyl-2-(3-methoxyphenyl)ethyl]piperazine dihydrochloride hemihydrate, melting point: 229°–234° C.

l-1-(2-Methoxyphenyl)-4-[1-phenyl-2-methoxyphenyl)ethyl]piperazine l-2'-nitrotartranilate hemihydrate, melting point: 84°–86° C.

d-1-(2-Methoxyphenyl)-4-[1-phenyl-2(3-hydroxyphenyl)ethyl]piperazine dihydrochloride hemihydrate, melting point: 181°–184° C.

REFERENCE EXAMPLE 1 dl-2-(3-Hydroxyphenyl)-1-phenylethylamine

A mixture of dl-2-(3-methoxyphenyl)-1-phenylethylamine hydrochloride (11.3 g), 48% hydrobromic acid (100 ml) and glacial acetic acid (30 ml) is refluxed for 4 hours. After the reaction, the solvent is distilled off. To the residue is added water and the mixture is made alkaline with ammonia and extracted with chloroform. The chloroform layer is dried over anhydrous potassium carbonate and the solvent is distilled off. To the residue is added ether. The precipitated crystals are separated by filtration and recrystallized from ethanol-ethyl acetate to give the desired compound (7.3 g), melting point: 179°–181° C.

REFERENCE EXAMPLE 2 d-2-(3-Hydroxyphenyl)-1-phenylethylamine

In 95% ethanol (5ml) are dissolved dl-2-(3-hydroxyphenyl)-1-phenylethylamine (3.2g) and l-2'-nitrotartranilic acid (4.2 g) with heating. After cooling, a mixture of ethyl acetic and ether is added thereto and the mixture is allowed to cool. The precipitated crystals are separated by filtration and fractionally recrystallized from ethanol to give d-2-(3-hydroxyphenyl)-1-phenylethylamine l-2'-nitrotartranilate (1.1 g), yellow needles, melting point: 159°–160° C., $[\alpha]_D^{28} = +3.3°$ (c=1.99, methanol).

REFERENCE EXAMPLE 3 dl-1-Phenyl-2-(3-tolyl)ethylamine (i) A solution of benzonitrile (58.5 g) in anhydrous ether (150 ml) is added dropwise with stirring to Grignard reagent which is prepared from magneisum turnings (14.6 g), a small amount of iodine and m-methylbenzylbromide (100 g) in anhydrous ether (800 ml) at moisture-free atmosphere. The mixture is refluxed for 6 hours. The reaction mixture is decomposed by adding water thereto, and the ether layer is separated and distilled to remove the solvent. The residue is mixed with 10% hydrochloric acid and the mixture is refluxed for 1.5 hours. After cooling, the mixture is extracted with ether. The ether layer is dried over anhydrus sodium sulfate and the solvent is distilled off to give crude m-methylbenzyl phenyl ketone (82 g).

(ii) A mixture of the m-methylbenzyl phenyl ketone obtained above (82 g) with ammonium formate (163 g) is heated with stirring at 185° C. for 3 hours. After cooling, water is added to the reaction mixture and the mixture is extracted with benzene. The benzene layer is dried over anhydrous sodium sulfate and the solvent is distilled off to give crude dl-N-formyl-1-phenyl-2-(3-tolyl)ethylamine (74 g).

(iii) A mixture of the N-formyl compound obtained above (74 g) with 17.5% hydrochloric acid (300 ml) is refluxed with stirring for 10 hours. After cooling, the reaction mixture is washed with ether and made alkaline with concentrated aqueous ammonia and extracted with chloroform. The chloroform layer is dried over anhydrous sodium sulfate, and the solvent is distilled off. The residue is distilled under reduced pressure to give colorless liquid (33 g), boiling point: 136°–139° C./1 mm Hg. The hydrochloride of this compound is prepared by treating the free base obtained above with ethanolic hydrochloric acid and followed by recrystallization thereof, melting point: 245°–248° C.

REFERENCE EXAMPLE 4 d-1-Phenyl-2-(3-tolyl)ethylamine

A mixture of dl-1-phenyl-2-(3-tolyl)ethylamine (33.0 g), L-aspartic acid (20.9) methanol (300 ml) and water (1200 ml) is warmed and dissolved. After cooling, the precipitated crystals are separated by filtration and fractionally recrystallized from a 20% methanol-water to give d-1-phenyl-2-(3-tolyl)-ethylamine L-aspartate (7.0 g), melting point: above 300° C., $[\alpha]_D^{28} = +49.1°$ (c=1.0 water).

The salt obtained above is treated with an alkali to give the free base thereof as colorless oily substance, $[\alpha]_D^{28} = +48.8°$ (c=2.0 methanol).

REFERENCE EXAMPLE 5 dl-N,N-bis(2-chloroethyl)-1-phenyl-2-(3-tolyl)-ethylamine (i) A solution of 3-(2-hydroxyethyl)-2-phenyloxazolidine (78 g) in anhydrous ether (300 ml) is added dropwise with stirring to Grignard reagent which is prepared from magnesium turnings (22 g) and m-methylbenzylbromide (150 g) in anhydrous ether (1200 ml), and the mixture is refluxed for 3 hours. After the reaction, the reaction mixture is decomposed with an ammonium chloride aqueous solution, and made alkaline with ammonia. The ether layer is separated and extracted with an excess amount of 10% hydrochloric acid. The aqueous layer is separated and made alkaline with sodium hydroxide and extracted with chloroform. The chloroform layer is dried over anhydrous sodium sulfate, and the solvent is distilled off to give crude dl-N,N-bis(2-hydroxyethyl)-1-phenyl-2-(3-tolyl)ethylamine (100 g) as an oily substance.

(ii) The dl-N,N-bis(2-hydroxyethyl)-1-phenyl-2-(3-tolyl)ethylamine (100 g) obtained above is dissolved in chloroform (150 ml) and thereto is added dropwise a solution of thionyl chloride (100 ml) in chloroform (50 ml), and the mixture is refluxed for 3 hours. After the reaction, the solvent and the excess of thionyl chloride are distilled off under reduced pressure to give the desired compound as hydrochloride (116 g) in the form of syrup.

REFERENCE EXAMPLE 6 dl-N,N-Bis(2-bromoethyl)-2-(3-hydroxyphenyl)-1-phenylethylamine (i) A solution of 3-(2-hydroxyethyl)-2-phenyloxazolidine (11.0 g) in anhydrous ether (30 ml) is added dropwise with stirring to Grignard reagent which is prepared from magnesium turnings (3.3 g) and m-methoxybenzyl chloride (20.7 g) in anhydrous ether (150 ml), and the mixture is refluxed for 3 hours. After the reaction, the reaction mixture is decomposed by adding water thereto. The ether layer is separated and extracted with 10% hydrochloric acid (100 ml). The hydrochloric acid layer is made alkaline with ammonia and extracted with ether. The ether layer is dried over anhydrous sodium sulfate, and the solvent is distilled off to give crude dl-N,N-bis(2-hydroxyethyl)-2-(3-methoxyphenyl)-1-phenylethylamine (12.7 g) as an oily substance. When this substance is recrystallized from ethanol, it shows a melting point of 67°–69° C.

(ii) The dl-N,N-bis(2-hydroxyethyl)-2-(3-methoxyphenyl)-1-phenylethylamine (12.7 g) obtained above is dissolved in chloroform (15 ml) and thereto is added two drops of dimethylformamide and further added dropwise a solution of thionly bromide (25 ml) in chloroform (15 ml) and the mixture is refluxed for 3 hours. After the reaction, the solvent and the excess of thionyl bromide are distilled off under reduced pressure. To the syrup-like residue (21 g) is added 47% hydrobromic acid (120 ml) and the mixture is mildly refluxed for 1 hour. Thereafter, the aqueous layer is separated by decantation and treated with charcoal and then distilled under reduced pressure to remove the solvent. To the residue is added acetone-benzene and then the solvent is distilled off to give the desired compound as hydrobromide (13.5 g) in the form of syrup.

REFERENCE EXAMPLE 7 dl-N-[2-(3-methoxyphenyl)-1-phenylethyl]piperazine (i) In dimethylformamide (60 ml) are dissolved dl-2-(3-methoxyphenyl)-1-phenylethylamine (8.6 g) and N-benzyl-2,2'-dichlorodiethylamine hydrochloride (10.2 g) and thereto is added sodium hydrogen carbonate (11.5 g). The mixture is refluxed with stirring for 8 hours. After cooling, the inorganic materials are filtered off. The filtrate is distilled to remove the solvent. To the residue is added aqueous ammonia and the alkaline mixture is extracted with ether. The ether layer is washed with water, dried over anhydorus sodium sulfate, and the solvent is distilled off. The residue is treated with ethanolic hydrochloric acid to give the hydrochloride, which is recrystallized from ethanol to give dl-1-benzyl-4-[2-(3-methoxyphenyl)-1-phenylethyl]piperazine dihydrochloride (9.0 g), melting point: 211°-214° C.

(ii) In acetic acid (70 ml) is dissolved dl-1-benzyl-4-[2-(3-methoxyphenyl)-1-phenylethyl]piperazine dihydrochloride (5.0 g) and thereto is added 5% palladiumcarbon (7.5 g), and the mixture is subjected to a catalytic reduction with heating. When about 300 ml of hydrogen is absorbed, the reaction is stopped and the catalyst is filtered off. The filtrate is distilled to remove the solvent. The residue is washed with ether, dissolved in water, made alkaline with a concentrated aqueous ammonia and extracted with chloroform. The chloroform layer is washed with water, dried over anhydrous sodium sulfate, and the solvent is distilled off. The oily residue is treated with ethanolic hydrochloric acid to give the hydrochloride, which is recrystallized from ethanol to give the desired compound as dihydrochloride sesquihydrate (3.0 g), melting point: 214°-218° C.

In the same manner as described above, the following compound are prepared.

dl-N[2-(3-Hydroxyphenyl)-1-phenylethyl]piperazine, free base: melting point: 219°-221° C. dihydrobromide sesquihydrate: melting point: 256°-258° C.

REFERENCE EXAMPLE 8 dl-1-(3-Methylcrotonyl)-4-[2-(3-hydroxyphenyl)-1-phenylethyl]piperazine

In methanol (300 ml) is dissolved dl-N[2-(3-hydroxyphenyl)-1-phenylethyl]piperazine (3.5 g) and thereto are added water (6 ml) and potassium carbonate (3.3 g). To the mixture is further added dropwise with stirring 3,3-dimethylacryloyl chloride (1.9 g) over a period of about 1 hour. The mixture is stirred at room temperature for 2 hours, and then the solvent is distilled off under reduced pressure. To the residue is added a 10% sodium carbonate aqueous solution and the mixture is extracted with chloroform. The chloroform layer is dried over anhydrous sodium sulfate, and the solvent is distilled off to give the desired compound (3.6 g), which is recrystallized from methanol to give coloress crystlas, melting point: 186°-187° C.

EXAMPLE 39

| 1-1-(3-Methyl-2-butenyl)-4-[2-(3-hydroxyphenyl)-1-phenylethyl]-piperazine dihydrochloride | 10 g |
|---|---|
| Starch | 150 g |
| Calcium carboxymethyl cellulose | 30 g |
| Hydroxypropyl cellulose | 9 g |
| Magnesium stearate | 1 g |

The above components are blended, granulated and made into tablets in accordance with the conventional method. Then 100 tablets each weighing 200 mg are formed.

EXAMPLE 40

| 1-1-Cyclohexyl-4-[1-phenyl-2-(3-tolyl)-ethyl]piperazine dihydrochloride | 10 g |
|---|---|
| Lactose | 100 g |
| Starch | 35 g |
| Talc | 5 g |

This formulation can make 1000 tablets. The tablets are formed on a 7.0 mm flat punch and the tablets may be coated, if desired.

What is claimed is:
1. A compound of the formula:

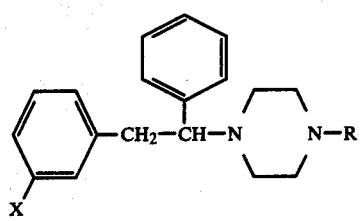

wherein X is hydroxy or an alkanoyloxy having from 2 to 5 carbon atoms; and R is an unsubstituted monocycloalkyl having from 5 to 8 carbon atoms, or a pharmacetuically acceptable salt thereof.

2. A compound according to claim 1, which is in the 2-form.

3. A compound according to claim 1, which is in dl form.

4. A compound of the formula:

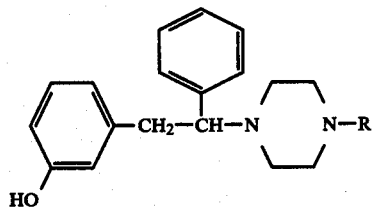

wherein R is an unsubstituted monocycloalkyl having from 5 to 8 carbon atoms, or a pharmaceutically acceptable salt thereof.

5. A compound according to claim 4 which is in the l-form.

6. A compound according to claim 4, which is in dl form.

7. 1-Cyclohexyl-4-[2-(3-hydroxyphenyl)-1-phenylethyl] piperazine, or a pharmaceutically acceptable salt thereof.

8. The compound according to claim 7, which is in dl-form.

9. The compound according to claim 7 which is in l-form.

10. A compound of the formula:

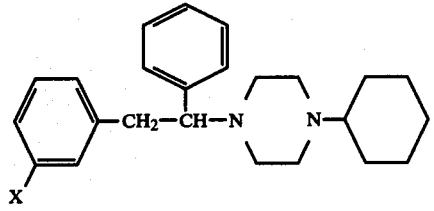

wherein X is hydroxy or an alkanoyloxy having from 2 to 5 carbon atoms, or a pharmaceutically acceptable salt thereof.

11. A compound according to claim 10, which is in the l-form.

12. A compound according to claim 10, which is in dl form.

13. An analgesic composition consisting essentially of an analgesic effective amount of the compound as set forth in claim 7, and a pharmaceutically acceptable carrier.

14. An analgesic composition consisting essentially of an analgesic effective amount of the compound as set forth in claim 8, and a pharmaceutically acceptable carrier.

15. An analgesic composition consisting essentially of an analgesic effective amount of the compound as set forth in claim 9, and a pharmaceutically acceptable carrier.

* * * * *